(12) United States Patent
Chana

(10) Patent No.: US 7,819,875 B2
(45) Date of Patent: Oct. 26, 2010

(54) SURGICAL DEVICES AND METHODS OF USE

(76) Inventor: Gursharan Singh Chana, Kenwood 57 Bracebridge Road, Sutton Coldfield (GB) B74 2SL ( * ) Notice: Subject to any disclaimer, the term of this patent is extended or adjusted under 35 U.S.C. 154(b) by 1154 days.

(21) Appl. No.: 10/503,788

(22) PCT Filed: Feb. 7, 2003

(86) PCT No.: PCT/GB03/00557

§ 371 (c)(1),
(2), (4) Date: Jan. 21, 2005

(87) PCT Pub. No.: WO03/065906

PCT Pub. Date: Aug. 14, 2003

(65) Prior Publication Data

US 2005/0131414 A1    Jun. 16, 2005

(30) Foreign Application Priority Data

Feb. 8, 2002 (GB) .................................. 0202934.6
Mar. 5, 2002 (GB) .................................. 0205043.3
Aug. 23, 2002 (GB) .................................. 0219696.2

(51) Int. Cl.
*A61B 17/58* (2006.01)
*A61B 17/60* (2006.01)
*A61F 2/00* (2006.01)

(52) U.S. Cl. .............................. 606/81; 606/80; 606/91; 606/99

(58) Field of Classification Search ............. 606/79–81, 606/91, 99; 623/22.11, 22.12, 22.21
See application file for complete search history.

(56) References Cited

U.S. PATENT DOCUMENTS 4,466,429 A    8/1984   Loscher (Continued)

FOREIGN PATENT DOCUMENTS

EP                1132051 A2       9/2001

(Continued)

OTHER PUBLICATIONS

Biomet, Inc.; Biomet, Inc. Catalog, published late 1980's in the U.S., p. B-2 seems to disclose a curved Impactor shaft (No. 424485) for use in hip replacement surgeries.

(Continued)

*Primary Examiner*—Thomas C Barrett
*Assistant Examiner*—Andrew Yang
(74) *Attorney, Agent, or Firm*—Neifeld IP Law, PC

(57) ABSTRACT

A surgical device for holding and rotating an acetabular reaming head is provided, comprising a shaft having a length which runs from a first end adapted for holding an acetabular reaming head to a second end. At least part of the shaft is divergent from the axis defined by the first and second ends of the shaft, for example the shaft may include a C-shaped divergent portion. A head held by the device can therefore access the acetabular in its true anatomical position while avoiding encroachment of the shaft on surrounding body parts.

45 Claims, 7 Drawing Sheets

U.S. PATENT DOCUMENTS

| | | | | |
|---|---|---|---|---|
| 4,528,980 A * | 7/1985 | Kenna | | 606/80 |
| 5,171,312 A * | 12/1992 | Salyer | | 606/81 |
| 5,176,711 A | 1/1993 | Grimes | | |
| 5,411,514 A | 5/1995 | Fucci | | |
| 5,474,560 A * | 12/1995 | Rohr, Jr. | | 606/91 |
| 5,851,208 A | 12/1998 | Trott | | |
| 5,916,231 A | 6/1999 | Bays | | |
| 5,951,561 A | 9/1999 | Pepper | | |
| 6,174,313 B1 * | 1/2001 | Bonutti | | 606/80 |
| 6,312,438 B1 * | 11/2001 | Adams | | 606/159 |
| 6,436,107 B1 | 8/2002 | Wang | | |
| 6,447,514 B1 | 9/2002 | Stalcup et al. | | |
| 6,451,058 B2 * | 9/2002 | Tuke et al. | | 623/22.21 |
| 6,475,221 B1 * | 11/2002 | White et al. | | 606/80 |
| 6,533,749 B1 | 3/2003 | Mitusina | | |
| 6,676,706 B1 * | 1/2004 | Mears et al. | | 623/22.4 |
| 7,008,430 B2 | 3/2006 | Dong | | |
| 7,326,215 B2 | 2/2008 | Myers | | |
| 2003/0050645 A1 | 3/2003 | Parker et al. | | |
| 2003/0130741 A1 * | 7/2003 | McMinn | | 623/23.14 |
| 2004/0087958 A1 * | 5/2004 | Myers et al. | | 606/80 |
| 2004/0111092 A1 * | 6/2004 | Penenberg | | 606/81 |
| 2005/0131414 A1 | 6/2005 | Channa | | |
| 2005/0216022 A1 | 9/2005 | Lechot | | |
| 2005/0222572 A1 | 10/2005 | Channa | | |
| 2008/0065081 A1 | 3/2008 | Lechot | | |

FOREIGN PATENT DOCUMENTS

| | | |
|---|---|---|
| FR | 1041311 | 1/1951 |
| JP | 05123334 | 5/1993 |
| JP | 05123334 A | 5/1993 |
| JP | 2001-293017 A | 10/2001 |
| WO | WO 03/065906 | 8/2003 |
| WO | WO 03/092513 | 11/2003 |

OTHER PUBLICATIONS

Unknown, Biomet, Inc., Biomet, Inc. Catalog published in the late 1980's in the U.S., p. B-2 seems to disclose a curved inpactor shaft (No. 424485) for use in hip replacement surgeries.

Aug. 14, 2003, PCT International Search Report PCT/GB03/00557.

May 11, 2004, PCT International Preliminary Exam Report PCT/GB03/00557.

Biomet, Inc.: Biomet, Inc. Catalog, published in the late 1980s in the U.S., p. B-2 seems to disclose a curved inpactor shaft (No. 424485) for use in hip replacement surgeries, Of Record.

Aug. 14, 2003, PCT International Search Report PCT/GB03/00557.

Nov. 13, 2006, Affidavit Under 37 CFR 1.131 filed with the USPTO during prosecution of U.S. Appl. No. 10/284,003, now USP 7,326,215.

May 12, 2004, International Preliminary Examination Report and International Search Report PCT/GB03/00557.

Aug. 20, 2008, Response to Official Communication filed in EP 03706689.1.

Mar. 3, 2006, English translation of notification of first office action in China application 038061899.

Aug. 20, 2008, Response dates Aug. 15, 2008 to Official Communication filed in EP 03706689.1, naming Channa as inventor.

Mar. 3, 2006, English translation of: notification of first office action, notification of second office action, and notification and text of 3rd office action, in China application 038061899, naming Channa as inventor.

Apr. 15, 2009, Examination Report in EPO application 03706689.1-2310, naming Channa as inventor.

Claims presented Feb. 8, 2008 in U.S. Appl. No. 11/935,198 naming Lechot as inventor.

Claims and arguments presented Oct. 20, 2008 in U.S. Appl. No. 11/123,932 naming Lechot as inventor.

Claims as originally filed in U.S. Appl. No. 11/123,932 to Lechot.

IDS filed in U.S. Appl. No. 11/123,932 to Lechot with the originally filed application, noting claims copied from Myers application U.S. Appl. No. 10/284,003, filed Oct. 30, 2002.

Third Office Action in CN application 03806189.9, naming Channa as inventor, English language translation in CN Office Action in national stage of Channa PCT application.

First Office Action in Cn application CN 03806189.9, naming Channa as inventor, English language translation in CN Office Action in national stage of Channa PCT application.

Fourth Office Action in CN application 03806189.9, naming Channa as inventor, English language translation in CN Office Action in national stage of Channa PCT application.

Second Office Action in CN application 03806189.9, naming Channa as inventor, English language translation in CN Office Action in national stage of Channa PCT application.

Claims in CN application 03806189.9, naming Channa as inventor., filed in response to fourth CN Office Action.

Apr. 15, 2009 Examination report and Annex and Apr. 25, 2008 Examination report and annex in EP application 03 706 689.1-2310, naming Channa as inventor.

First Office Action in JP application 2003-565,336, naming Channa as inventor, No translation.

Translation of first Office Action in JP application 2003-565,336.

Oct. 22, 1953, English translation of text of French Patent 1041311.

Nov. 13, 2006, Affidavit Under 37 CFR 1.131, dated Jul. 11, 2006, filed with the Uspto during prosecution of U.S. Appl. No. 10/284,003, now USP 7,326,215.

IDS filed in 11/123,932 to Lechot with the originally filed application, noting claims copied from Myers application U.S. Appl. No. 10/284,003, filed Oct. 30, 2002.

English translation of the issues raised by the Examiner in KR application corresponding to U.S. Appl. No. 10/503,788.

* cited by examiner

SURGICAL DEVICES AND METHODS OF USE

The present invention relates to improved surgical devices and their uses, in particular a surgical reaming device for use in the removal of bone tissue and methods for its use. The improved reaming device is particularly for use in reducing invasion when carrying out hip replacement and hip resurfacing surgery.

Procedures for replacement of all or part of a patient's joint have been in existence for a number of years. The current procedures generally require large incisions to be made through the skin and underlying tissue of the patient to allow the surgeon to access and see the joint while the surgery is being carried out.

For example to carry out hip replacement or hip resurfacing surgery an incision approximately 25-30 cm must be made through the skin and underlying tissue. Such an incision allows good visibility of the joint and the surgery can therefore be carried out using the naked eye. Furthermore current surgical devices such as reaming devices, impactors and pushers used in surgery such as hip replacement and his resurfacing require good access to the joint which is provided by a large incision.

Reaming devices generally comprise a rotating cutting portion situated at the end of an elongate drive shaft and connected to a power source. Reaming devices are used in hip replacement and hip resurfacing surgery to remove bone tissue from the acetabulum before a prosthetic acetabular cup is fitted. Pushers and impactors are used in the fitting or prosthetic joint components such as acetabular cups to the acetabulum.

Posterior access to a hip joint is usual during surgery and, as a result to obtain sufficient access to the joint a large amount of muscle tissue must be divided, cut through or separated from the bone to which it is anchored. This division or separation of the muscle allows the femoral head to be moved away from the acetabulum to allow access to the acetabulum, for example with a reaming device, or to allow removal of the femoral head. The division or separation of muscle is essential in the current methods for resurfacing a hip joint where the femoral head is not removed and access to the joint is therefore reduced.

Muscles such as the gluteus maximus and gluteus medius are usually cut through, divided or separated from the bone to which they are attached during hip surgery as are the tensor fascia lata and the ilio-tibial tract. Although the muscles do repair themselves following surgery the recovery period, in and out of hospital, and the amount of physiotherapy required is extensive. It is also possible that the muscles may never regain the strength they had before surgery. Furthermore cutting through muscles can lead to a significant loss of blood and the patient may require a blood transfusion.

Therefore there remains a need for surgical device and associated methods for their use that reduce the size of the incision required, the amount of muscle tissue cut through or separated from the bone to which it was attached and the access required to a joint to perform surgery.

According from a first aspect the present invention provides a surgical device suitable for use in hip surgery comprising a shaft having a first end and a second end, with the shaft being adapted at the first end to be connected to a head, wherein at least part of the length of the shaft is divergent from the axis formed between the first end and the second end of the shaft.

Specifically, a surgical device for holding and rotating an acetabular reaming head is provided, comprising a shaft having a length which runs from a first end to a second end, wherein the first end is adapted for holding an acetabular reaming head, the first and second ends defining an axis which runs through these two end points, wherein at least part of the shaft is divergent from said axis, allowing a head held by the device to access the acetabulum in its true anatomical position while avoiding encroachment of the shaft on surrounding body parts.

Preferably at least part of the length of the shaft is permanently divergent from the axis which runs through the first end and the second end of the shaft.

Preferably the part of the length of the shaft that is divergent from the axis which runs through the first end and the second end of the shaft is substantially C-shaped or includes a substantially C-shaped section. Accordingly, in a preferred aspect the invention provides a surgical device for holding and rotating an acetabular reaming head comprising a shaft having a length which runs from a first end to a second end, wherein the first end is adapted for holding an acetabular reaming head and wherein the shaft includes a substantially C-shaped portion along its length.

Preferably, the part of the shaft that is divergent from the axis forms a C-shape.

In surgery such as hip resurfacing surgery the provision of a substantially C-shaped portion or other divergent portion along the length of the drive shaft allows a reaming head to achieve access to the acetabulum without fully anteriorly displacing the femoral head and neck. In hip resurfacing surgery this removes the head to cut through large amounts of muscle tissue to allow the femoral head and neck to be displaced out of the acetabulum before reaming can take place.

The avoidance of the need to cut through large amounts of muscle and displace the femoral head and neck results in a much less invasive approach allowing a smaller incision through the skin and underlying tissue to be made. The muscle damage to the patient is greatly reduced therefore meaning that the patient can be mobilized much earlier than with existing resurfacing surgical methods, perhaps even on the same day as the surgery takes place. The amount of rehabilitation time required in hospital is less, reducing cost and increasing patient throughout. In some cases rehabilitation centres may be needed by patients but the time and attention required by patients in these facilities will also be less than with existing surgical methods.

In hip replacement surgery the removal of the femoral head from the femoral neck prior to reaming the acetabulum increases the access to the acetabulum when compared to resurfacing surgery. However the use of the surgical device of the present invention facilitates reaming as it avoids encroachment of the surgical device on to the femoral shaft. The use of the surgical device of the present invention therefore provides the same improvements in hip replacement surgery as it provides in hip resurfacing surgery.

The use of the surgical device of the present invention also allows reaming to take place in the true anatomical position of the acetabulum.

The shaft of the surgical device may be any suitable drive shaft that permits transmission of torque. The shaft may be selected from known torque transmitting mechanisms and devices such as a nickel titanium shaft, a flexible round or flat wire wound cable, a series of gear driven shafts or a series of shafts interconnected by universal joints.

Preferably, the shaft of the surgical device is connectable at the first end to a reaming head and at the second end to a rotational drive element. More preferably the surgical device comprises a rotatable drive shaft connectable at a first end to a reaming head and connected at a second end to a rotational drive element.

Alternatively a rotational drive element can be positioned adjacent the first end of the shaft so that in use it is located between the first end of the shaft and the reaming head.

The rotational drive element may be a manual drive element such as a handle to turn; alternatively the drive element may be an electrical power source. Most preferably the rotational drive element is an air powered or battery powered rotating drive element. The drive element must provide high torque at a low speed for maximum efficiency.

The rotational drive element may be provided with one or more gears.

It is preferred that a section of the shaft adjacent the first end is straight and a section of the shaft adjacent the second end is straight, and these straight sections are aligned with one another.

In a preferred embodiment the shaft has a substantially C-shaped portion and the section of the drive shaft between the substantially C-shaped portion and the first end that is connectable to the reaming head is straight and of sufficient length to ensure that eccentric motion of the drive shaft where it causes rotation of a reaming head is prevented. It is however also preferred that this section is not so long that this section encroaches on the femur or femoral shaft when in use.

Preferably the section of the drive shaft between the substantially C-shaped portion and the first end that is connectable to a reaming head and the section of the drive shaft between the substantially C-shaped portion and the second end are both straight. It is further preferred that these two sections are in line with each other as this allows accurate guidance of the reaming head.

A protective sleeve may, preferably, surround the drive shaft. In one embodiment, the drive shaft is held to the protective sleeve; for example with a series of bearings, which keep the drive shaft from riding on the inside of the housing. The protective sleeve is preferably made from metal, most preferably stainless steel. The protective sleeve is preferably made from cannulated material. The protective sleeve shields the drive shaft from body tissue during use and also shields the body tissue from damage by the rotating drive shaft.

The protective sleeve may comprise two or more sleeve members that are separable from each other, e.g. to allow cleaning. Such sleeve members may be connected by any suitable means. For example, the drive shaft may include at one end a capture mechanism adapted to receive an end of each of the housing members and align them in the correct position, and at its other end a ring adapted to interact with a catch in one of the housing members so as to retain the housing members in a connected formation.

The surgical device is preferably provided with a handle, suitable for manipulation by a surgeon. The handle may be provided as part of the shaft at the end furthest from the reaming head. In a preferred embodiment the handle is formed as part of the sleeve in which the drive shaft rotates.

The surgical device may be adapted at the first end of the shaft to connect to a reaming head by the provision of any suitable connecting means. The surgical device may be adapted so that the reaming head may be connected to the sleeve of the drive shaft by any suitable connecting means.

One preferred connecting means is the provision of one or more spring-biased pins and corresponding apertures, one part of the connecting means being provided on each of a neck extending from a base of a reaming head and the sleeve of the drive shaft. Another preferred connecting means is a bayonet mechanism, preferably with the bayonet fitting being provided on the end of the drive shaft. An alternative connecting means is a ball and cage mechanism.

The use of a simple connecting means allows the reaming head to be easily removed from the surgical device, e.g. for cleaning or for exchange of the head for a different sized head.

The present invention also provides, in a second aspect, a surgical instrument for acetabular reaming comprising a surgical device of the first aspect, as defined above, and an acetabular reaming head; wherein the acetabular reaming head is attached to the first end of the surgical device.

The reaming head can be any suitable reaming head depending on the use and the patient; a cheese grater type of reaming head is most preferred. This type of reaming head collects reamed material within the reaming head. Generally a number of reaming heads will be used in succession beginning with a small size and increasing in size until a sufficient amount of material has been removed for an acetabular cup to be fitted.

The reaming head may be connected to the surgical device, in particular to the sleeve of the drive shaft, by any suitable connecting means, such as those discussed above.

The base of the reaming head may suitably be detachable from the cutting portion of the reaming head to enable the reaming head to be emptied after use. The base of the reaming head may be attached to the cutting portion by any conventional means.

The use of a simple connecting means allows the instrument to be easily taken apart, e.g. for cleaning.

Accordingly, in one embodiment a surgical instrument suitable for acetabular reaming is provided comprising a shaft having a first and a second end, with the shaft being connected at the first end to a head, and with the first and second ends defining an axis which runs through these two end points, wherein at least part of the shaft is divergent from said axis, allowing the head to access the acetabulum in its true anatomical position while avoiding encroachment of the shaft on surrounding body parts.

Preferably, the part of the shaft that is divergent from the axis is substantially C-shaped or includes a substantially C-shaped section.

The surgical instrument provided may be a reaming instrument comprising a shaft connected at a first end to a reaming head, with at least part of the length of the shaft being divergent from the axis formed between the first end and the second end of the shaft, and with the reaming head being connected to a rotational drive element.

It is preferred that the shaft of the reaming instrument includes a substantially C-shaped portion along its length.

Preferably, the reaming instrument comprises a rotatable drive shaft connected at a first end to the reaming head and connected at a second end to a rotational drive element.

In a third aspect the invention provides a kit for performing hip surgery on a patient, comprising a surgical device in accordance with the first aspect described above; and one or more acetabular reaming heads having selected sizes, each operable with the first end of the surgical device for shaping the acetabular cavity of the patient.

The kit is preferably adapted in perform hip re-surfacing surgery.

Preferably, the kit further comprises one or more acetabular cup prostheses, selectable for implantation into the prepared cavity.

In accordance with the present invention a surgical instrument may also be provided which is a pusher suitable for pressurising a cemented acetabular cup into position in an acetabulum. The pusher comprises a shaft having a length and being connected at a first end to a pusher head, with at least part of the length of the shaft being divergent from the axis formed between the first end and the second end of the shaft. Preferably, a substantially C-shaped portion is included along the length of the shaft.

A pusher is used to push a cemented acetabular cup into a prepared acetabulum and hold it in place under manual pressure until the cement has cured.

The pusher head and shaft may be integral or alternatively the head may be secured to the shaft by any of the connection means set out above or by any other suitable means. The head is preferably made from a suitable material, such as metal or plastic material. The shaft is preferably rigid and is also preferably provided with a handle at the end further from the head.

The kit may therefore also suitably comprise a pusher as described above. Specifically, the kit may further comprise a pusher comprising a shaft having a length which runs from a first, insertion end adapted for holding a selected prosthesis, to a second end, the first and second ends defining an axis which runs through these two end points, wherein at least part of the shaft is divergent from said axis.

In accordance with the present invention a surgical instrument may also be provided which is an impactor suitable for use in impacting an uncemented acetabular cup into position in an acetabulum. The impactor comprises a shaft having a length and being connected at a first end to an impactor head, with at least part of the length of the shaft being divergent from the axis formed between the first end and the second end of the shaft. Preferably, a substantially C-shaped portion is included along the length of the shaft.

An impactor is used to impact an uncemented acetabular cup into a prepared acetabulum using force applied to the free end of the shaft.

The impactor head may be secured to the shaft by any of the connection means set out above, for example by means of a universal connector, or by any other suitable means. Alternatively, the impactor head and shaft may be intergral. The head is preferably made from a suitable material, such as metal or plastic material and is preferably provided with means to secure it to the acetabular cup during impacting.

The shaft is preferably rigid. The shaft is also preferably provided with a handle at the end furthest from the head.

The kit may therefore also suitably comprise an impactor as described above. Specifically, the kit may further comprise an impactor comprising a shaft having a length which runs from a first, impaction end adapted for holding a selected prosthesis, to a second end, the first and second ends defining an axis which runs through these two end points, wherein at least part of the shaft is divergent from said axis.

It is clearly preferred that for any pusher or impactor instruments used the section of the shaft between the substantially C-shaped portion and the first end of the shaft is straight. It is also preferred that this section is relatively short, such that this section does not encroach on the femur or femoral shaft when in use. Preferably the section of the shaft between the substantially C-shaped portion and the first end of the shaft and the section of the shaft between the substantially C-shaped portion and the second end of the shaft are both straight. It is further preferred that these two sections are in line with each other as this allows for accurate guidance.

It is also preferred that at least part of the length of the shaft of any pusher or impactor instruments used is permanently divergent from the axis which runs through the first end and the second end of the shaft.

The provision of a substantially C-shaped portion or other divergent portion along the length of the shaft of such pusher or impactor instruments allows access of the head of the surgical device to the acetabulum without full anterior displacement of the femoral head and neck to assist in the fitting of an acetabular cup.

In a fourth aspect a surgical instrument is provided which is an osteophyte remover suitable for use in removing peripheral acetabulum osteophytes. The osteophyte remover comprises a shaft connected at a first end to an osteophyte remover head, with at least part of the length of the shaft being divergent from the axis formed between the first end and the second end of the shaft. Preferably, a substantially C-shaped portion is included along the length of the shaft.

Accordingly, the invention provides an osteophyte remover instrument for use in removing peripheral acetabulum osteophytes comprising a shaft having a first and a second end, with the shaft being connected at the first end to an osteophyte remover head, with the first and second ends defining an axis which runs through these two and points, wherein at least part of the shaft is divergent from said axis, allowing the head to access the acetabulum in its true anatomical position while avoiding encroachment of the shaft on surrounding body parts. Preferably, the part of the shaft that is divergent from the axis is substantially C-shaped or includes a substantially C-shaped section. More preferably, the part of the shaft that is divergent from the axis is a C-shape.

Preferably at least part of the length of the shaft is permanently divergent from the axis which runs through the first end and the second end of the shaft.

It is preferred that the section of the shaft between the substantially C-shaped portion and the first end of the shaft, which is connected to the osteophyte remover head, is straight. It is also preferred that this section is relatively short, such that this section does not encroach on the femur or femoral shaft when in use.

The osteophyte remover head may be any head suitable for removing peripheral osteophytes. Preferably the head comprises a hemispherical portion and a disc portion, with the hemispherical portion having a smaller radius than the disc portion. The hemispherical portion is located centrally on one face of the disc portion such that a section of the face is left exposed around the hemispherical portion, said section having substantially uniform width.

The hemispherical portion is preferably releasably secured to the disc portion. The hemispherical portion may suitably be secured to the disc portion by means of a screw, for example the hemispherical portion may be provided with a screw in the centre of its base, and the disc portion provided with a correspondingly shaped threaded hole in the centre of one face to allow the hemispherical portion to be screwed into the disc portion.

Preferably the hemispherical portion is smooth and has the same radius as the cavity that has been reamed. The disc portion is provided with a serrated section for removing peripheral osteophytes. It is preferred that a serrated section is provided on at least part of, and preferably most of, the area of the face to which the hemispherical portion is secured which is not covered by the hemispherical portion. However, a smooth section is preferably provided around the periphery of the face, of substantially constant width. Further, the disc portion preferably has smooth edges.

In one embodiment, the disc portion is provided with a centrally located circular serrated section on one face, with a ring shaped smooth section being provided around the circular section, extending to the edge of the face. The edges of the disc portion are smooth. A hemispherical portion having a radius smaller than that of the circular section is secured centrally to said face of the disc, so as to leave a ring of serrated surface around its periphery, with a ring of smooth surface being provided around the periphery of the serrated ring, extending to the edge of the face.

The peripheral osteophyte remover is preferably provided with a rotational drive element for rotating the osteophyte remover head. The rotational drive element may be a manual drive element such as a handle to turn. Alternatively, the drive element may be an electrical power source. Most preferably the rotational drive element is an air powered or battery powered rotating drive element. The drive element must provide high torque at a low speed for maximum efficiency. The rotational drive element may be provided with one or more gears.

A peripheral osteophyte remover is used to remove peripheral osteophytes from the acetabulum after a cavity has been reamed. The remover is provided with an osteophyte remover head comprising a hemispherical portion having a radius approximately the same as the radius of the cavity that has been reamed, and a disc portion having a radius bigger than the radius of the cavity that has been reamed. The osteophyte remover head is positioned in the cavity and is rotated, thus causing peripheral osteophyte to be removed by the serrated part of the disc portion, whilst the smooth periphery of the disc portion prevents damage to the soft tissue. The shape of the shaft allows positioning in the true anatomical position, and therefore only the minimum required amount of peripheral osteophyte is removed.

The osteophyte remover head may be secured to the shaft by any of the connection means set out above, for example by means of a universal connector, or by any other suitable means. Alternatively, the osteophyte remover head and shaft may be integral.

A protective sleeve preferably surrounds the rotatable drive shaft. In one embodiment, the drive shaft is held to the protective sleeve; for example with a series of bearings, which keep the drive shaft from riding on the inside of the housing. Most preferably the drive shaft rotates within the sleeve. The protective sleeve is preferably made from metal, most preferably stainless steel. The protective sleeve is preferably made from cannulated material. The protective sleeve shields the drive shaft from body tissue during use and also shields the body tissue from damage by the rotating drive shaft.

The protective sleeve may comprise two or more sleeve members that are separable from each other, e.g. to allow cleaning. Such sleeve members may be connected by any suitable means. For example, the drive shaft may include at one end a capture mechanism adapted to receive an end of each of the housing members and align them in the correct position, and at its other end a ring adapted to interact with a catch in one of the housing members so as to retain the housing members in a connected formation.

The provision of a substantially C-shaped portion or other divergent portion along the length of the shaft of the osteophyte remover allows access of the head of the surgical instrument to the acetabulum without full anterior displacement of the femoral head and neck to assist in the removal of peripheral osteophytes after reaming.

The kit of the present invention, as described above, may therefore also suitably comprise an osteophyte remover instrument as described above. Specifically, the kit of the present invention may further comprise an osteophyte remover instrument for use in removing peripheral acetabulum osteophytes comprising a shaft having a first and a second end, with the shaft being connected at the first end to an osteophyte remover head, with the first and second ends defining an axis which runs through these two end points, wherein at least part of the shaft is divergent from said axis, allowing the head to access the acetabulum in its true anatomical position while avoiding encroachment of the shaft on surrounding body parts.

The present invention provides, in a fifth aspect, a method for performing hip surgery on a patient, comprising the steps of:
 a) providing a surgical device for holding and rotating an acetabular reaming head in accordance with the first aspect as described above;
 b) providing an acetabular reaming head and mounting the head on the first end of the device; and
 c) accessing the acetabulum of the patient with the surgical device, in its anatomical position of anteversion while avoiding encroachment on surrounding body parts, and reaming the acetabulum with the reaming head.

It is preferred that steps a)-c) are adapted to perform a hip re-surfacing surgery.

The shaft of the device provided in step a) is preferably surrounded by a sleeve that is C-shaped where the shaft is divergent from the axis. It is also preferred that the shaft of the device provided in step a) has a drive element coupled to the second end. In on embodiment, the shaft of the device provided in step a) is coupled to a drive element between the first end and the head.

It is preferable that the section of the shaft adjacent the first end and the section of the shaft adjacent the second end are aligned with one another. In one embodiment of the method, the femoral head is disclosed from the acetabulum being reamed in step c).

The method for performing hip surgery on a patient, preferably comprises the steps of:
 a) providing a surgical device for holding and rotating an acetabular reaming head according to the first aspect of the invention as defined above;
 b) providing an acetabular reaming head and attaching the head to the first end of the device;
 c) accessing the acetabulum of the patient with the surgical device, in its anatomical position of anteversion while avoiding encroachment on surrounding body parts, and reaming the acetabulum with the reaming head;
 d) providing an acetabular prosthesis;
 e) providing a surgical device comprising a shaft having a length which runs from a first, securement end to a second end, the first and second ends defining an axis which runs through these two end points, wherein at least part of the shaft is divergent from said axis; and
 f) attaching the prosthesis to the securement end and delivering the prosthesis into the acetabulum along the insertion axis while avoiding encroachment on surrounding body parts.

In the method it is preferred that step c) further comprises making a posterior incision that splits the fibers of the gluteus maximus of the patient, anteriorly to their insertion in the ilio-tibial tract.

In one embodiment, the device of step e) is a pusher and the prosthesis of steps e) and f) is a trial or definitive cemented component. In an alternative embodiment, the device of step e) is an impactor and the prosthesis of steps e) and f) is a trial or definitive cementless component.

The present invention also provides, in a sixth aspect, a method for performing a total hip replacement comprising the steps of:
 (a) making a posterior incision;
 (b) performing a femoral neck osteotomy;
 (c) preparing the acetabulum to receive an acetabular cup by reaming the acetabulum with a surgical instrument for acetabular reaming according to the second aspect of the invention as defined above;

(d) securing an acetabular cup in the acetabulum;

(e) preparing the femur to receive a femoral stem; and (f) securing a femoral stem to the femur.

Using the surgical instruments of the present invention in a total hip replacement avoids the possibility of the instrument encroaching on the shaft of the femur.

Preferably, in step (d) a device is used comprising a shaft having a length which runs from a first end adapted for holding an acetabular cup, to a second end, the first and second ends defining an axis which runs through these two end points, wherein at least part of the shaft is divergent from said axis. For example, an instrument such as a pusher as described above or an impactor as described above may be used.

The present invention further provides, in a seventh aspect, a method for resurfacing a hip joint comprising the steps of:

(a) making a posterior incision;

(b) preparing the acetabulum to receive an acetabular cup by reaming the acetabulum with a surgical instrument for acetabular reaming according to the second aspect of the invention as defined above, without fully anteriorly displacing the femoral head; and (c) securing an acetabular cup in the acetabulum.

Using the surgical instrument of the present invention in hip resurfacing avoids the possibility of the instrument encroaching on the shaft of the femur and allows access to the acetabulum without full anterior displacement of the femur.

Preferably, in step (c) a device is used comprising a shaft having a length which runs from a first end, adapted for holding an acetabular cup, to a second end, the first and second ends defining an axis which runs through these two end points, wherein at least part of the shaft is divergent from said axis. For example, an instrument such as a pusher as described above or an impactor as described above may be used.

Although the optimum method for carrying out hip replacement or hip resurfacing surgery according to the present invention includes the use of the surgical devices and/or instruments of the present invention it is possible to reduce invasion connected with hip surgery using conventional equipment using a surgical technique according to the present invention. For maximum reduction of invasion it is preferred to use the devices and/or instruments of the present invention and the surgical methods of the present invention.

The present invention also provides a method for performing a total hip replacement comprising the steps of:

making a posterior incision positioned such that the fibres of the gluteus maximus are split anteriorly to their insertion in the ilio-tibial tract;

performing a femoral neck osteotomy;

preparing the acetabulum to receive an acetabular cup by reaming the acetabulum;

securing an acetabular cup in the acetabulum;

preparing the femur to receive a femoral stem;

securing a femoral stem to the femur.

The present invention further provides a method for resurfacing a hip joint comprising the steps of:

making a posterior incision positioned such that the fibres of the gluteus maximum are split anteriorly to their insertion in the ilio-tibial tract;

preparing the acetabulum to receive an acetabular cup by reaming the acetabulum; and securing an acetabular cup in the acetabulum.

The posterior incision preferably begins at a distance of Xcm down from the tip of the greater trochanter. Xcm is the distance from the tip of the greater trochanter to the point of bisection of the lateral cortex by a line down the centre of the femoral neck. The incision extends at an angle of 40-50°, most preferably 45° to the femoral shaft. The incision preferably extends proximally and posteriorly to the femoral shaft. The incision is preferably 5 to 12 cm, for example 7 to 12 cm, more preferably 5 to 10 cm in length, for example 8 to 10 cm.

The position of the incision allows the fibres of the gluteus maximus to be split along the incision resulting in the fibres being split anteriorly to their insertion in the ilio-tibial tract and the ilio-tibial tract is not incised.

In the replacement and resurfacing surgery the acetabular cup is preferably fitted using the pusher and/or impactor devices as defined above.

In the replacement and resurfacing surgery a step of removing peripheral osteophytes from the acetabulum is preferably included, after the reaming step and before the step of fitting the acetabular cup. This step is preferably carried out using the peripheral osteophyte remover according to the fourth aspect of the invention.

The present invention also provides, in an eighth aspect, a method for removing peripheral osteophytes from an acetabulum after a cavity has been reamed in said acetabulum, comprising the steps of:

a) providing an osteophyte remover instrument for use in removing peripheral acetabulum osteophytes according to the fourth aspect of the invention as defined above; and b) positioning the osteophyte remover head in the cavity, while avoiding encroachment of the instrument on surrounding body parts, and removing peripheral osteophyte from the cavity by rotating the osteophyte remover head in the cavity.

Except where clearly indicated to the contrary by the wording used, all of the preferred and optional features of each aspect of the invention may be used in combination with one or more of any of the other preferred or optional features.

Embodiments of the invention will now be described in detail with reference to the drawings in which.

DEVICES OF THE PRESENT INVENTION

Figure 1:
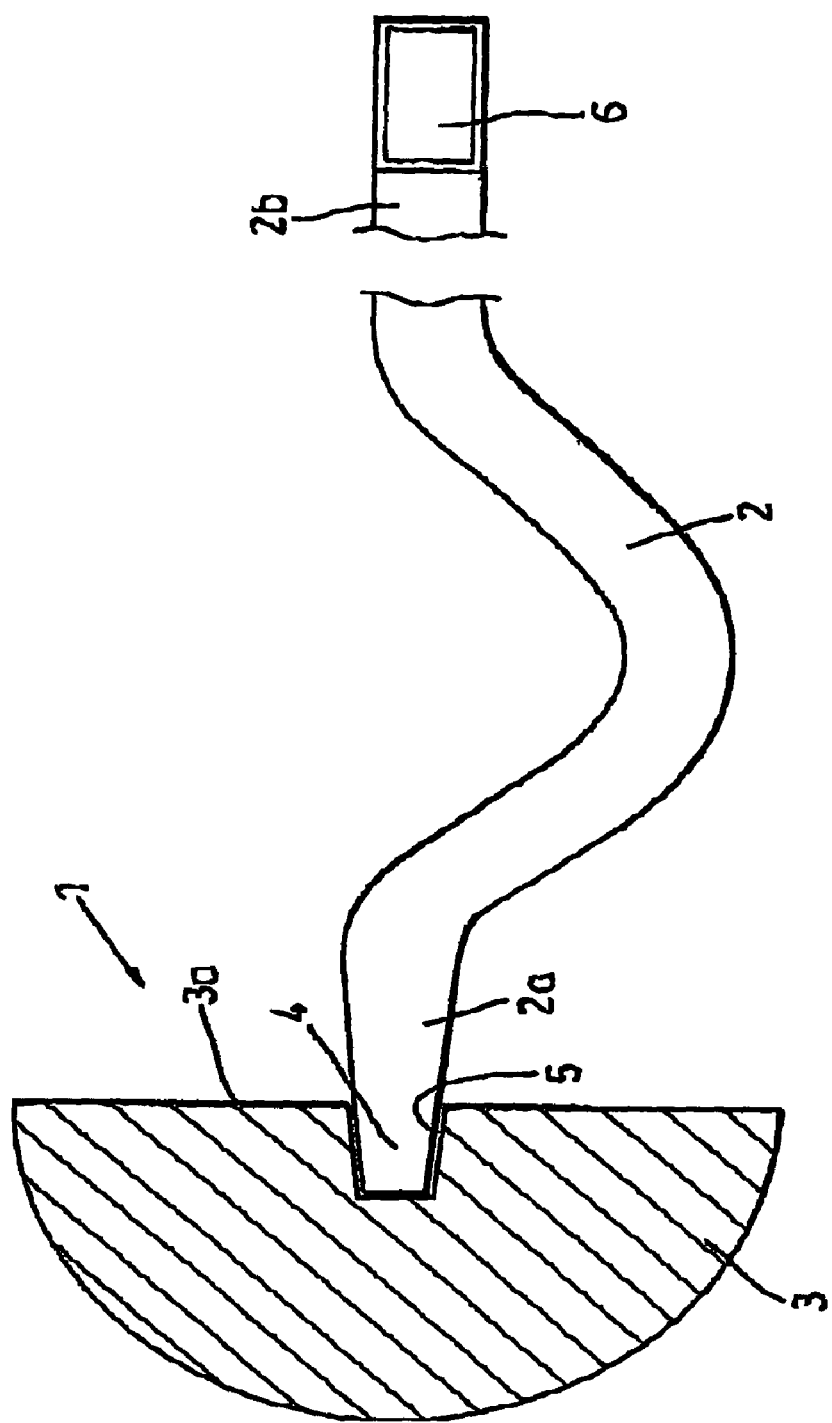
FIG. 1 shows a cross section along the length of a pusher or impactor as used in the present invention.

FIG. 1 shows a pusher/impactor instrument as used in the present invention. The instrument 1 comprises a rigid, substantially C-shaped, shaft 2 having a head 3 connected to a first end 2a of the shaft 2. The head 3 is connected to the shaft 2 by a tapered portion 4 of the first end of the shaft 2a being received in a corresponding aperture 5 in the base 3a of the head 3. The shaft is provided with a handle 6 at the end 2b of the shaft furthest from the head 3.

The head 3 may be any suitable head for impacting or pushing an acetabular cup (not shown) into the acetabulum of a hip joint (not shown).

Figure 2:
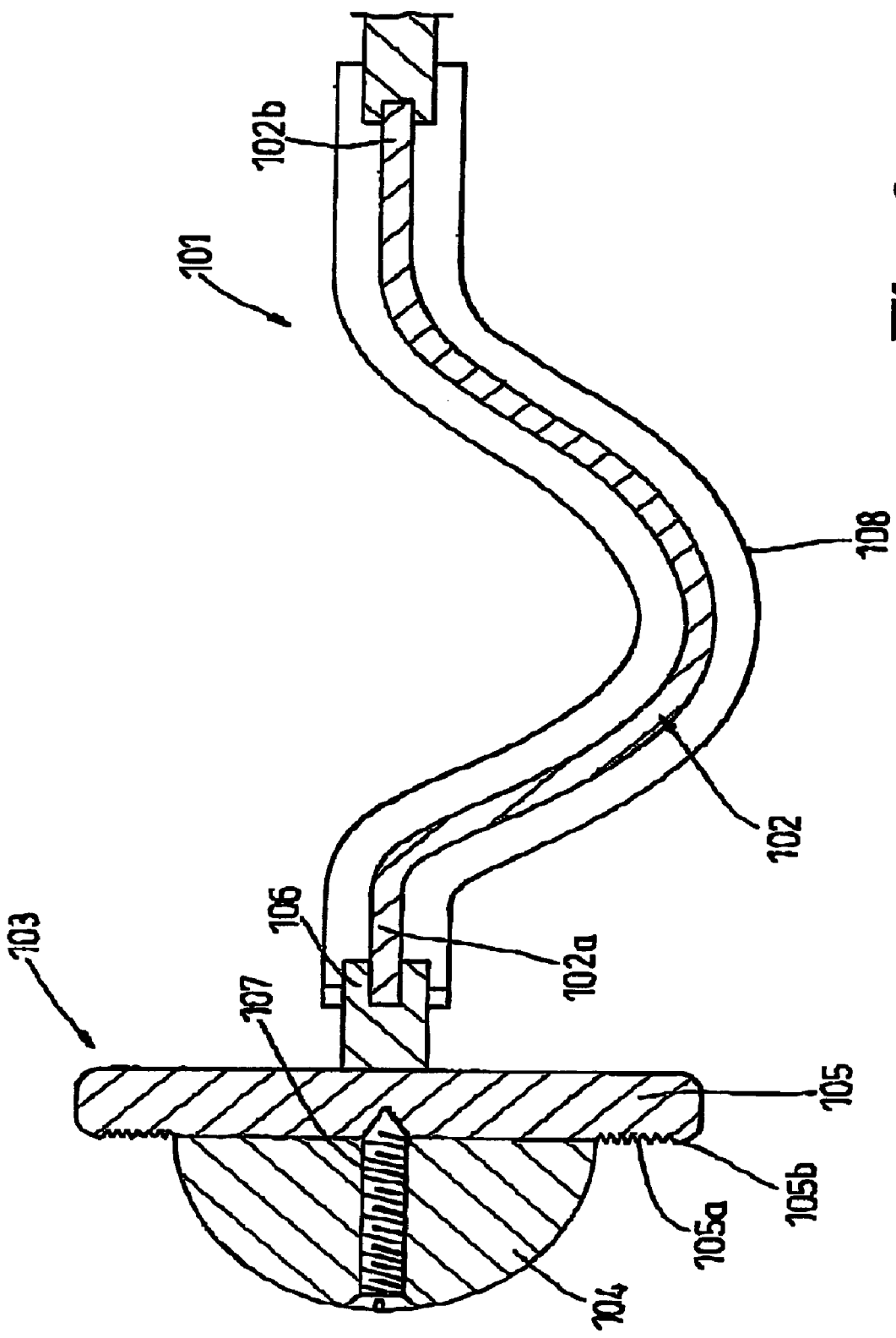
FIG. 2 shows a cross section along the length of a peripheral osteophyte remover according to the present invention.

FIG. 2 shows a peripheral osteophyte remover instrument according to the present invention. The instrument 101 comprises a shaft 102 having a head 103 connected to a first end 102a of the shaft 102. The drive shaft 102 is housed in a stainless steel sleeve 108 within which the drive shaft 102 is free to rotate. The sleeve 108 has a substantially C-shaped portion positioned near the head 103 and a straight handle portion extending from the C-shaped portion away from the head 103. A further straight portion is provided extending from the substantially C-shaped portion towards the head 103 in line with the handle portion.

The head 103 comprises a hemispherical portion 104 and a disc portion 105. The hemispherical portion 104 has a radius smaller than that of the disc portion 105, and is located centrally on a first face of the disc portion 105, being secured by means of a screw 107. A serrated section 105a is provided on the face of the disc portion 105 to which the hemispherical portion is secured, covering most of the area of said face that is not covered by the hemispherical portion 104. However a smooth section 105b of substantially constant width is provided around the periphery of the face. The disc portion 105 has smooth edges.

The first end 102a of the drive shaft 102 is received by an adapter 106 extending from the centre of the disc portion 105. The shaft 102 is provided with a rotatable drive element (not shown) at the end 102b of the shaft furthest from the head 103. The first end 102a of the drive shaft 102 must be well secured in the adapter 106 to prevent eccentric rotation of the drive shaft at the end 102a. The drive shaft 102 must cause true rotation of the head 103 through adapter 106.

Figure 3:
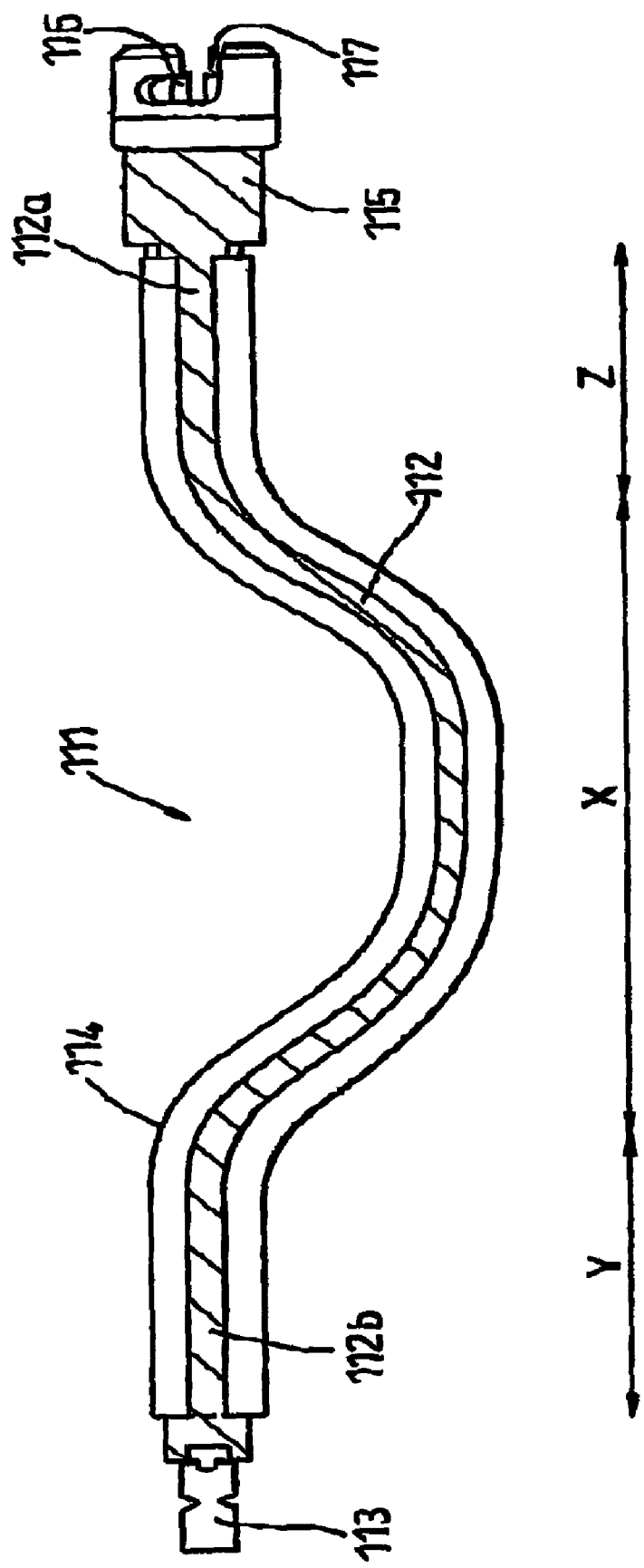
FIG. 3 shows a cross section along the length of a surgical device for holding and rotating a reaming head according to the present invention.

FIG. 3 shows a surgical device 111 for holding and rotating a reaming head according to the present invention. The device 111 comprises a rotatable drive shaft 112, which is a rotatable steel power cable, providing rotation and flexibility. The first end 112a of the drive shaft 112 is adapted so as to be connectable to a reaming head. The second end 112b of the drive shaft 112 is provided with a drive fitting 113, which is adapted to be linked to a rotary power source.

The first end 112a connects to a reaming head by a bayonet style mechanism. Accordingly, the first end 112a is provided with a slide 115 carrying a pin component 116 of the bayonet mechanism. The pin 116 co-operates with a catch 117 provided at the end of the device 111, to form a bayonet that can capture a reaming head. This mechanism allows a reaming head to be securely attached but also easily removed, either for replacement with a different sized reaming head or for cleaning.

The drive shaft 112 is housed in a stainless steel sleeve 114 within which the drive shaft 112 is free to rotate. The sleeve 114 has a substantially C-shaped portion X positioned near the first end 112a and a straight handle portion Y extending from the C-shaped portion away from the first end 112a. A further straight portion Z is provided extending from the substantially C-shaped portion X towards the first end 112a in line with the handle portion Y.

The substantially C-shaped portion X allows the reaming device 111 to pass through a miniature incision in the skin without impinging on the skin and to easily access the acetabulum without the need to fully anteriorly displace the femoral head or without encroaching on to the femoral shaft. The straight portion Y provides a handle by which to manoeuvre the device and the straight portion Z prevents eccentric rotation of the drive shaft where it causes rotation of a head connected to the first and of the shaft. The straight portion Y and Z are in line to allow accurate guidance of an attached reaming head.

Figure 4:
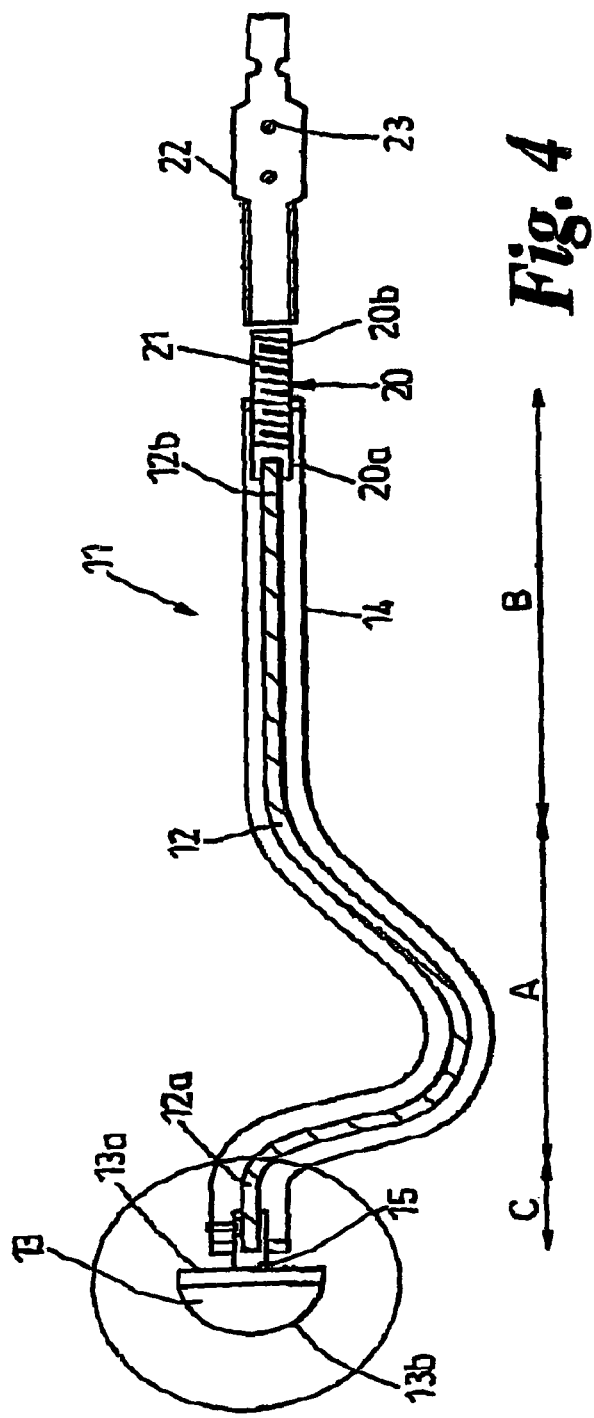
FIG. 4 shows a cross section along the length of a surgical reaming instrument according to the present invention.

FIG. 4 shows a surgical reaming instrument 11 according to the present invention. The instrument 11 comprises a rotatable drive shaft 12, which is a rotatable steel power cable, providing rotation and flexibility. The instrument 11 also comprises a head 13, which is connected to a first end 12a of the drive shaft 12. The head 13 comprises a base portion 13a and a cutting portion 13b. A rotatable drive element (not shown) is connected to the second end 12b of the drive shaft 12.

The drive shaft 12 is housed in a stainless steel sleeve 14 within which the drive shaft 12 is free to rotate. The sleeve 14 has a substantially C-shaped portion A positioned near the head 13 and a straight handle portion B extending from the C-shaped portion away from the head 13. A further straight portion C is provided extending from the substantially C-shaped portion A towards the head 13 in line with the handle portion B.

The substantially C-shaped portion A allows easy access of the reaming instrument 11 to the acetabulum without the need to fully anteriorly displace the femoral head or without encroaching on to the femoral shaft. The straight portion B provides a handle by which to manoeuvre the instrument and the straight portion C prevents eccentric rotation of the drive shaft where it causes rotation of the head 13. The straight portions B and C are in line to allow accurate guidance of the head 13.

The first end 12a of the drive shaft 12 is received by a neck 15 extending from the centre of the base 13a of the reaming head 13. The first end 12a of the drive shaft 12 must be well secured in the neck 15 to prevent eccentric rotation of the drive shaft at the end 12a. The drive shaft 12 must cause true rotation of the head 13 through neck 15.

Figure 4A:
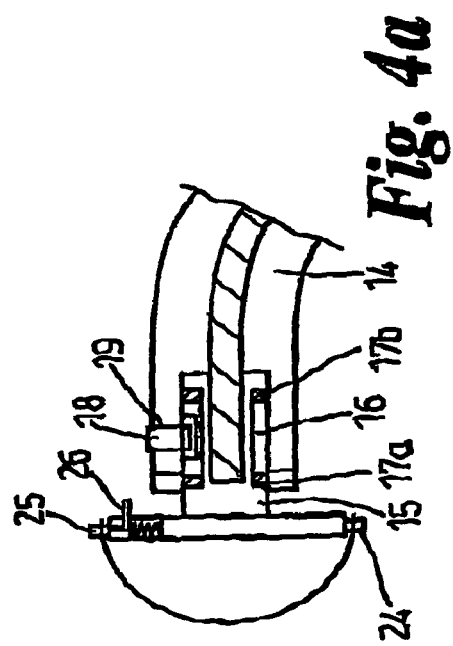
FIG. 4a shows an enlarged view of an area of the instrument shown in FIG. 4.

The neck 15 is provided with a freely rotating collar 16 held in position around the neck 15 by two further collars 17a, 17b fixedly attached to the neck 15 (see FIG. 4a). Bearing surfaces are provided between the neck 15 and the collar 16. The head 13 is secured to the sleeve 14 by means of a spring-biased lug 18 on the collar 16 being received within a corresponding aperture 19 provided through the sleeve 14. The lug and aperture lock the collar 16 in a fixed position within the sleeve 14, within which the neck 15 is free to rotate. The lug 18 can be disengaged from the aperture 19 by applying pressure through the aperture on to the lug against the action of the spring.

The second end 12b of the drive shaft is connected to a first end 20a of a connector 20. The drive shaft 12 is secured to the connector 20 such that eccentric rotation is prevented. The connector 20 is provided with an externally screw thread portion 21 at the second end 20b. The connector 20 is secured by the external screw threaded portion 21 to an internally screw threaded connector 22 for connection to an air powered drive element (not shown) suitable for providing high torque at a low speed. The connector 22 is sized to fit partially into the sleeve 14 and has a bearing surface to allow it to rotate within the sleeve 14. Grub screws 23 can be used to further secure the connector 22 in position with respect to drive shaft 12.

The cutting portion 13b can be any suitable cutting portion for a reaming head depending on the patient and the required result, for example suitable cutting portions are cheese grater cutting portions for a reaming head. The cutting portion 13b is secured to the base 13a of the head 13 by means of a fixed projection 24 and a spring-biased projection 25 situated diametrically opposite each other around the rim of base 13a engaging corresponding apertures on the rim of the cutting portion. The spring-based projection 25 can be retracted into the base 13a by means of lever 26. This is a standard fixing mechanism for a cutting portion of a reaming head to be secured to the base.

The reaming instrument 11 is assembled by feeding the drive shaft 12 into the sleeve 14 with the connector 20 being fed through first. Aperture may be provided on the bends of the sleeve 14 to allow the use of a poker to help the connector 20 pass round the bends in the sleeve 14. The neck 15 of the head 13 is secured into a first end of the sleeve 14 by means of the spring-biased lug 18. The connector 22 is secured to the connector 20 by means of the corresponding screw threads and the grub screws 23. The connector 22 is then secured to a rotatable drive element and an appropriate reaming head is secured to the base 13a.

In use the power source causes rotation of the connectors 22 and 20 and of the drive shaft 12 within the protective sleeve 14. This action results in rotation of the neck 15 and the attached reaming head about an axis X extending longitudinally through the straight portions C and B. The neck 15, the connector 20 and the straight portions C and B of the sleeve 21 ensure that true rotation is transmitted along the length of the drive shaft 12 from the power source to the head 13.

Figure 5:
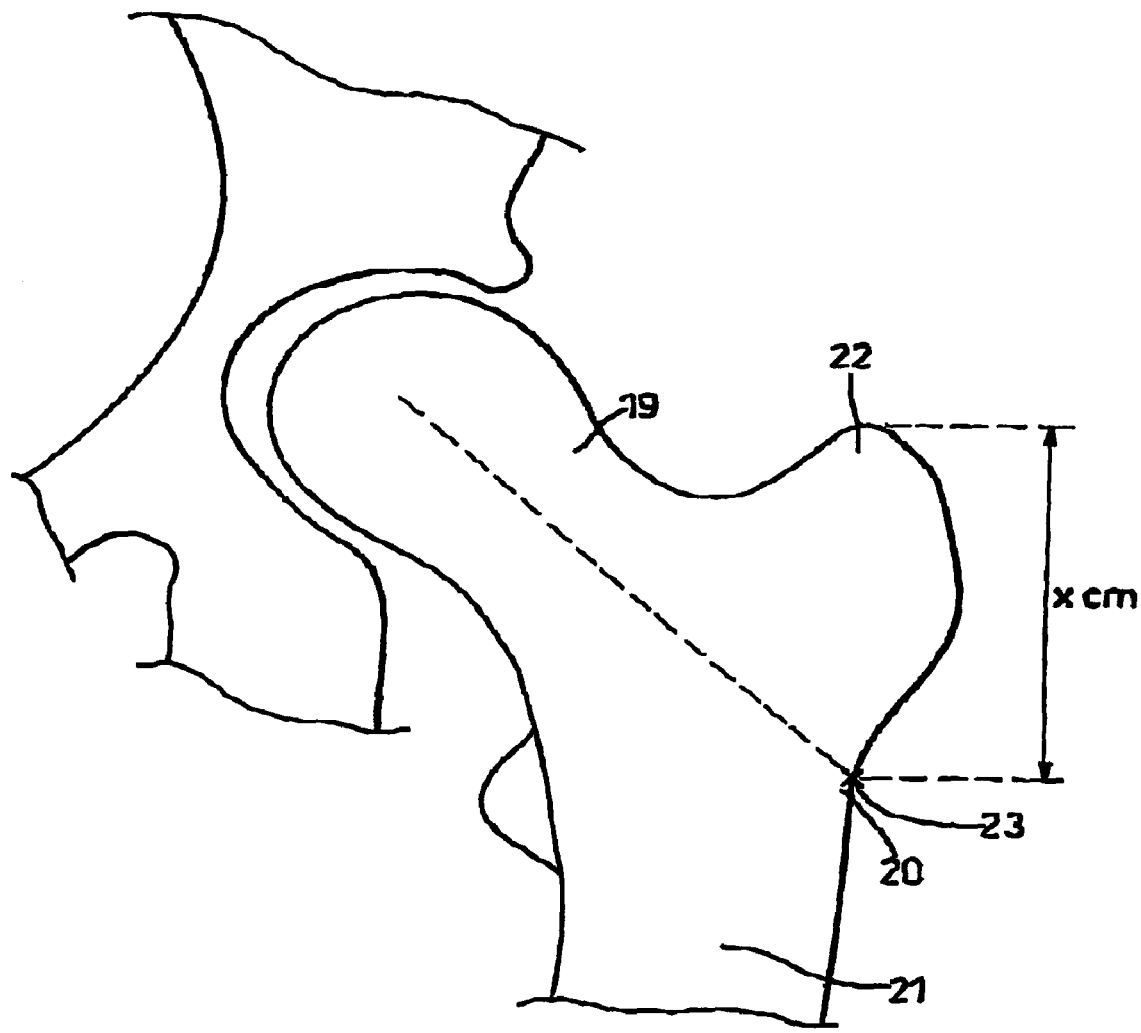
FIG. 5 shows a cross section through a human hip joint based on an AP radiograph.

Methods for Carrying out Hip Surgery using the Devices of the Present Invention 1) Pre-Operative Planning From a plain AP radiograph of the patient's hip joint (shown in FIG. 5) a line is drawn down the centre of the femoral neck 19 to bisect the lateral cortex 20 of the femur 21 at a point 23 usually just below the greater trochanter 22. The distance (x cm) from this point of bisection 23 to the tip of the greater trochanter is measured (usually 5-8 cm with average of 6 or 7 cm).

2) Technique

Anaesthetic

General or spinal anaesthetic with 3 in 1 femoral nerve block using 30 ml of plain 0.25% Bupuvicane.

Position

True lateral position

Incision

Figure 6:
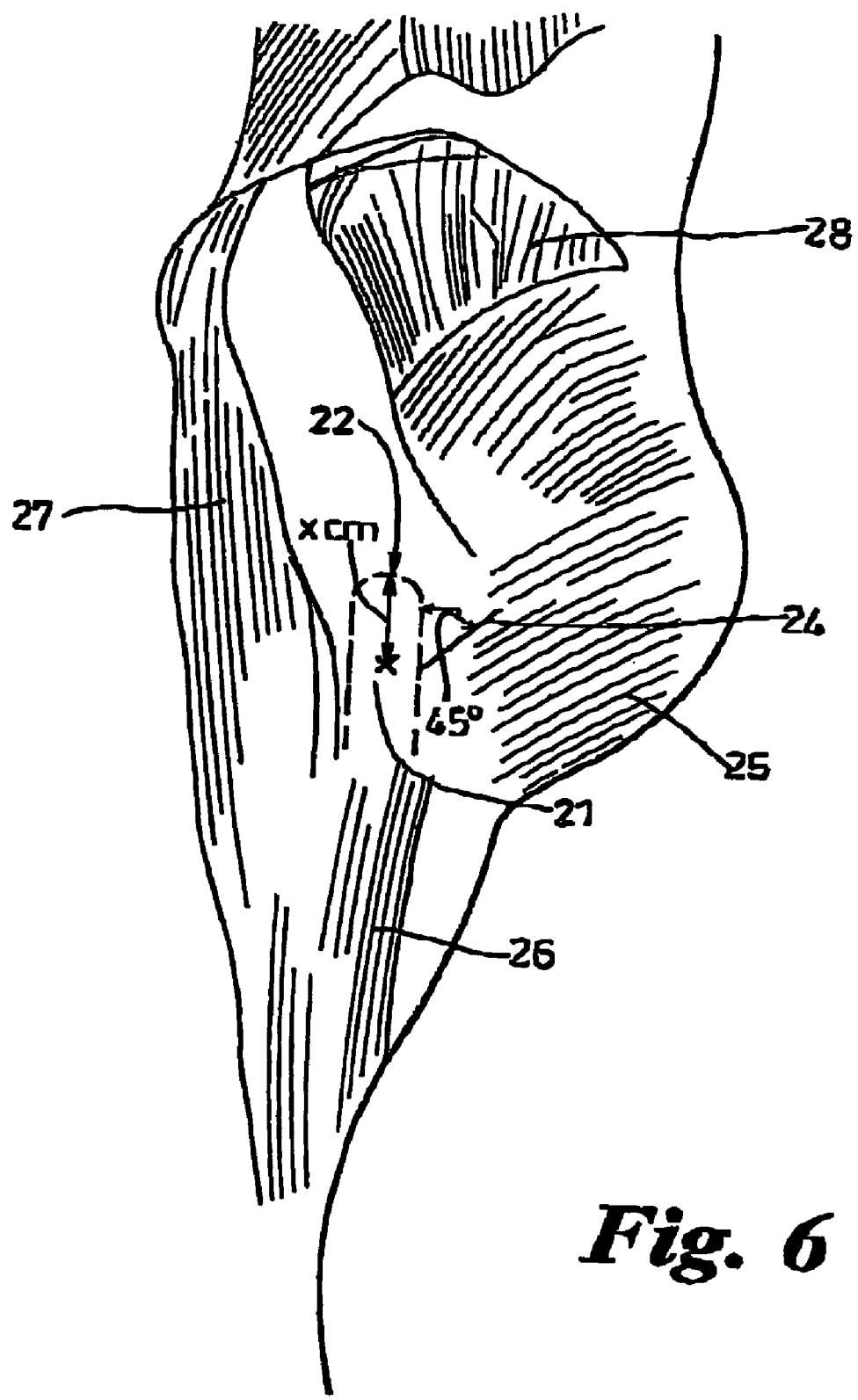
FIG. 6 shows a cross section through the lower part of a human body showing the major muscle groups around the hip joint.

FIG. 6 shows the main muscle groups around the hip joint which are the gluteus maximus 25, the ilio-tibial tract 26, the tensor fascia lata 27 and the gluteus medius 28. Using a sterile marker pen, the position of the greater trochanter 22 is marked and using a ruler point 'x' is marked on the skin x cm (usually 6 or 7 cm) distal to the greater trochanter tip to locate the mid femoral neck line bisection point 23 on the femur. Skin incision 24 is started from the posterior border of the femur at the point 'x' going proximally and posteriorly at an angle of 45° to the femoral shaft 21 for 8-10 cm. The incision 24 will be in line with the fibres of the gluteus maximus 25. The subcutaneous tissue is incised along this line and the fibres of gluteus maximus 25 are split along the whole length of the incision 24. The gluteus maximus fibres 25 are split anteriorly to their insertion to ilio-tibial tract 26 and the ilio-tibial tract 26 is not incised at all.

Figure 7:
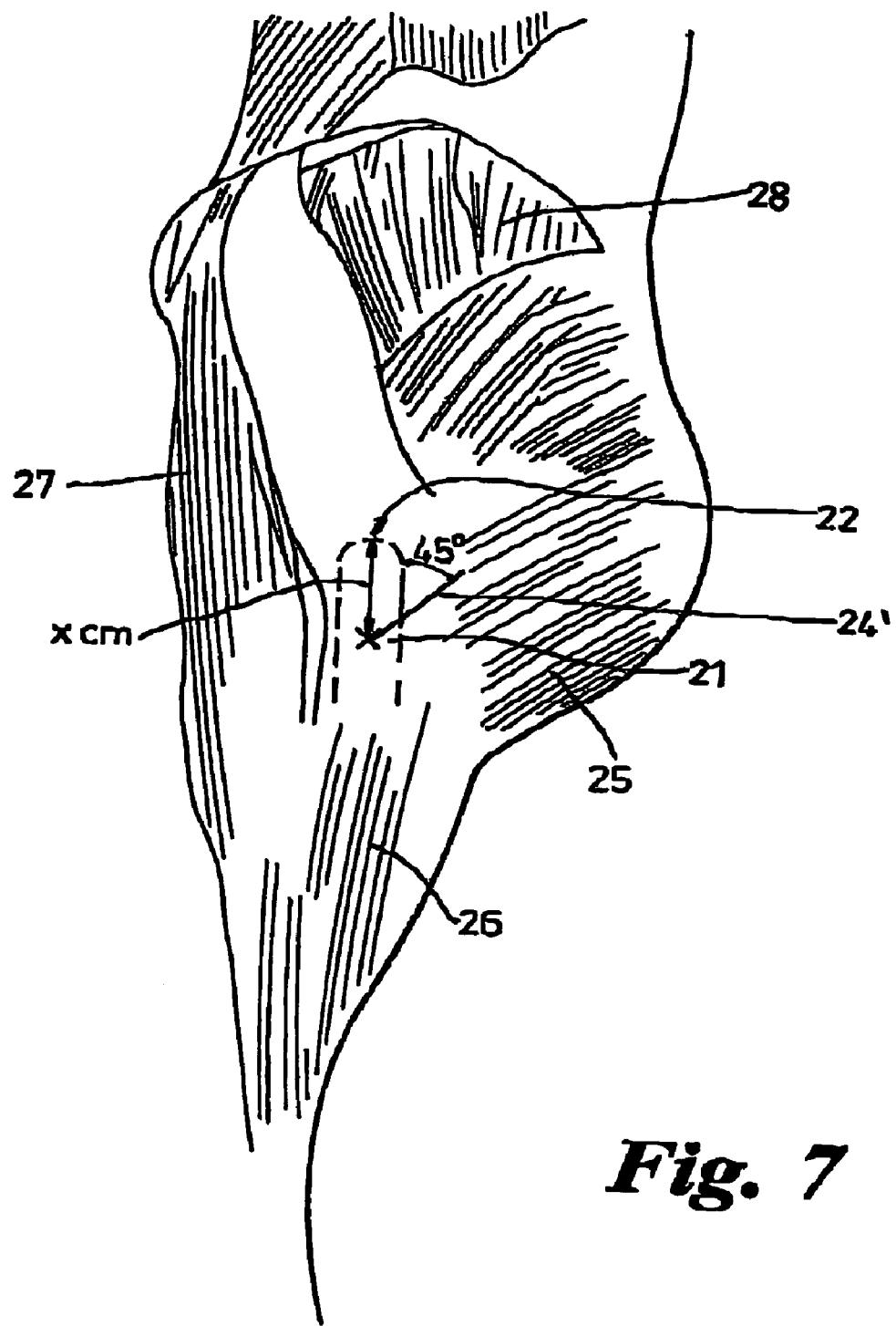
FIG. 7 shows a cross section through the lower part of a human body showing the major muscle groups around the hip joint.

FIG. 7 shows the main muscle groups around the hip joint which are the gluteus maximus 25, the ilio-tibial tract 26, the tensor fascia lata 27 and the gluteus medius 28. In a variation of the method described in relation to FIG. 6, using a sterile marker pen, the position of the greater trochanter 22 is marked and using a ruler point 'x' is marked on the skin x cm (usually 6 or 7 cm) distal to the greater trochanter tip to locate the mid femoral neck line bisection point 23 on the femur. Skin line 24' is marked from point 'x' going proximally and posteriorly at an angle of 45° to the femoral shaft 21. A skin incision is made along the line 24'. The skin incision is started 4 cms posterior to the posterior border of femur 21 along line 24' and extended along this line giving an initial incision of 5 cm. The incision along line 24' will be in line with the fibres of the gluteus maximus 25. The incision can be extended on either end if needed depending on the size of the patient. The subcutaneous tissue is incised along this line 24' and the fibres of gluteus maximus 25 are split along the whole length of the incision on line 24'. The gluteus maximus fibres 25 are split anteriorly to their insertion to ilio-tibial tract 26 and the ilio-tibial tract 26 is not incised at all.

Minimal bleeding occurs in these approaches as the incision is at the watershed of the superior and inferior gluteal vessels. The gluteus maximus muscle is retracted at right angles to its fibres and adipose tissue overlying the short external rotators of the hip will be exposed. The adipose tissue is cleared to expose the short external rotators of the hip. Thorough haemostasis is carried out of the vessles around the insertion of the short external rotators. The pirlformis, inferior and superior gemalli are divided at their insertion and a stay suture applied to the cut ends. Retraction of the short external rotators posteriorly will prevent injury to the sciatic nerve. The quadratus femoris is released from its femoral insertion. This will expose the posterior capsule of the hip joint. A thorough superior, posterior and inferior capsulotomy of the hip is performed and the hip dislocated. With forceful internal rotation of the hip, it is possible to carry out anterior capsulotomy of the joint. Flexion of the knee to 90° will allow relaxation of the ilio-tibial tract 26. Note that in internal rotation the split gluteus maximus fibres 25 will tend to 'snap shut'.

3a) For Total Hip Replacement Arthroplasty

Femoral neck osteotomy is performed. This will allow easy access to the acetabulum. Further completion of circumferential capsulotomy is carried out. Release of capsule is then performed. A Homan retractor is inserted supero-anteriorly to the acetabulum and the femur displaced anteriorly. A Styles nail is inserted into the ischium, just posterior to the acetabular rim. Another Homan retractor is inserted inferiorly peripheral to the transverse ligament for tissue retraction inferiorly. This will give a good access to the acetabulum. Acetabular reaming in its anatomical position of anteversion is facilitated with the substantially C-shaped reaming instrument of the present invention as there will not be any encroachment of the reaming instrument drive shaft to the femur. The acetabular preparation is completed and the cemented or uncemented component is secured in the usual manner. A substantially C-shaped pusher is used to pressurize the acetabular component for the cemented component, alternatively a substantially C-shaped impactor is used to impact an uncemented acetabular component. Once the acetabular component is secured, peripheral acetabular osteophytes are removed. The femur is prepared next. To allow easy access to the femoral shaft the hip is flexed to 45°, internally rotated by 90° and adducted by 30-40° to allow delivery of the osteotomised base of femoral neck. The femur is prepared and the trial femoral component is inserted. The hip is reduced and checked for stability. A definitive femoral component is cemented/inserted.

Closure

The short external rotators and quadratus femoris muscles are sutured back on to the femur. A drain is inserted in the wound and brought proximally. The gluteus maximus fascia is closed over the drain. If necessary a second drain can be inserted in the fatty layer and the wound closed in layers.

3b) For Hip Resurfacing

In view of the fact that the gluteus maximus tends to 'snap shut' the anterior hip capsulotomy is carried out with alternate retraction of proximal and distal aspect of the gluteus maximus split. The hip can be put in extremes of internal rotation, adduction and flexion to allow 'delivery' of the femoral head into the wound. Usually the femoral head can be delivered into the wound at 90° of internal rotation, 45° of flexion and as much adduction as possible. Partial release of gluteus maximus insertion to the femur may be required in larger patients. The femoral head and neck are measured for sizing of femoral head component. The femoral head guide wire is inserted with the centralising femoral head jig. The femoral head cuts are completed in the usual manner up to the stage ready to implant the femoral component. Any femoral head bone grafting or cementing holes are not done at this stage. With the overall size of the femoral head reduced at this stage the femoral head can easily be displaced to lie deep to the gluteus medius with the hip in neutral position. This will allow further thorough anterior capsular release to be carried out. With the femur in a more neutral position the gluteus maximus will be relaxed. A supero-anterior Homan retractor, a Styles nail in the ischium and a Homan retractor inferiorly will give adequate exposure to the acetabulum. As gluteus maximus insertion to the femur is not released in most patients, displacement anteriorly of the femur is not fully possible. For this reason normal acetabular reaming devices cannot be used as they will not allow reaming in the anatomical anteversion position of the acetabulum. Therefore the substantially C-shaped reaming instrument is used to ream the acetabulum. The substantially C-shaped part of the reaming instrument will allow reaming in the true anatomical position of the acetabulum. The acetabular trial shaft will also have a substantially C-shaped configuration and also the definitive insertor of the acetabular component will have a substantially C-shaped configuration to allow impaction of the acetabular component. After completion of the trial acetabular component the definitive acetabular component is impacted into position. All peripheral acetabular osteophytes can be removed at this stage. The Styles nail is removed and all the Homan retractors are removed. The hip is internally rotated to 90°, flexed to 45° and adducted to allow delivery of the femoral head. A 3 mm vent drill hole is made into the lesser trochanter to vent the femur. A drainage cannula is inserted into the vent hole in the lesser trochanter and connected to suction. The femoral neck is surrounded with a split swab or special drapes and final preparation of the femoral head is carried out including femoral head grafting or drilling of the femoral head drill holes for cementation. The femoral head is dried and the definitive femoral component is cemented. All excess cement is cleared and the hip reduced. Routine closure of the wound is carried out as described above.

4) Post Operative Regime

In the immediate post-operative period a check x-ray is carried out. Adequate analgesia is maintained and after 6-8 hours the patient can stand up with a Zimmer frame. The following day the drains are removed and the patient mobilised with a Zimmer frame. The patient should be able to transfer to a step down/rehabilitation facility if the haemoglobin check is of satisfactory level. When the patient can be discharged from the step down facility to home environment depends on social circumstances and agility of the patient.

The invention claimed is:

1. A surgical instrument for acetabular reaming comprising:
   a surgical device for holding and rotating an acetabular reaming head comprising a drive shaft having a length which runs from a first end to a second end,
   wherein said shaft comprises a first straight portion, a second straight portion, and an intermediate portion between said first straight portion and said second straight portion;
   wherein said first straight portion and said second straight portion are in line with one another and aligned along an axis defined by a line running through said first end and said second end;
   wherein said intermediate portion is permanently divergent from said axis, thereby allowing a head held by the device to access the acetabulum in its true anatomical position while avoiding encroachment of the drive shaft on surrounding body parts;
   wherein the first end is adapted for holding an acetabular reaming head; and
   an acetabular reaming head;
   wherein the acetabular reaming head is attached to the first end of the surgical device.

2. The instrument of claim 1 wherein the reaming head is a cheese grater type of reaming head.

3. The instrument of claim 1 wherein the reaming head has a base and a cutting portion and the base of the reaming head is detachable from the cutting portion of the reaming head.

4. A surgical instrument suitable for acetabular reaming comprising:
   a drive shaft having a first end and a second end, said first end and said second end defining an axis passing there through;
   a head connected to said drive shaft at said first end;
   wherein said drive shaft comprises a first straight portion, a second straight portion, and an intermediate portion between said first straight portion and said second straight portion;
   wherein said first straight portion and said second straight portion are aligned along said axis; and
   wherein said intermediate portion is permanently divergent from said axis, thereby allowing said head to access the acetabulum in its true anatomical position while avoiding encroachment of said drive shaft on surrounding body parts.

5. The instrument of claim 4 wherein the part of the drive shaft that is divergent from the axis is substantially C-shaped or includes a substantially C-shaped section.

6. A kit for performing hip surgery on a patient, comprising:
   a) a surgical device for holding and rotating an acetabular reaming head comprising a drive shaft having a length which runs from a first end to a second end, said first end and said second end defining an axis passing there through;

wherein said first end is adapted for holding an acetabular reaming head;

wherein said drive shaft comprises a first straight portion, a second straight portion, and an intermediate portion between said first straight portion and said second straight portion;

wherein said first straight portion and said second straight portion are in line with one another and aligned along said axis;

wherein said intermediate portion is permanently divergent from said axis, thereby allowing a head held by the device to access the acetabulum in its true anatomical position while avoiding encroachment of the drive shaft on surrounding body parts; and b) one or more acetabular reaming heads having selected sizes, each operable with the first end of the surgical device for shaping the acetabular cavity of the patient.

7. The kit of claim 6, further comprising:
c) one or more acetabular cup prostheses, selectable for implantation into the prepared cavity.

8. The kit of claim 6, further comprising:
d) a pusher instrument comprising a shaft having a length which runs from a first, insertion end adapted for holding a selected prosthesis, to a second end, the first and second ends defining an axis which runs through these two end points, wherein at least part of the shaft is divergent from said axis.

9. The kit of claim 6, further comprising:
e) an impactor instrument comprising a shaft having a length which runs from a first, impaction end adapted for holding a selected prosthesis, to a second end, the first and second ends defining an axis which runs through these two end points, wherein at least part of the shaft is divergent from said axis.

10. The kit of claim 6 wherein the kit is adapted to perform hip resurfacing surgery.

11. A kit according to claim 6, further comprising an osteophyte remover instrument for use in removing peripheral acetabulum osteophytes comprising a shaft having a first and a second end, with the shaft being connected at the first end to an osteophyte remover head, with the first and second ends defining an axis which runs through these two end points, wherein at least part of the shaft is permanently divergent from said axis, allowing the head to access the acetabulum in its true anatomical position while avoiding encroachment of the shaft on surrounding body parts.

12. A method for performing hip surgery on a patient, comprising the steps of:
a) providing a surgical device for holding and rotating an acetabular reaming head comprising a drive shaft having a length which runs from a first end to a second end, wherein the first end is adapted for holding an acetabular reaming head, the first and second ends defining an axis which runs through these two end points;

wherein said drive shaft comprises a first straight portion, a second straight portion, and an intermediate portion between said first straight portion and said second straight portion;

wherein said first straight portion and said second straight portion are in line with one another and aligned along said axis;

wherein said intermediate portion is permanently divergent from said axis, thereby allowing a head held by the device to access the acetabulum in its true anatomical position while avoiding encroachment of the drive shaft on surrounding body parts;

b) providing an acetabular reaming head and attaching the head to the first end of the device;

c) accessing the acetabulum of the patient with the surgical device, in its anatomical position of anteversion while avoiding encroachment on surrounding body parts, and reaming the acetabulum with the reaming head;

d) providing an acetabular prosthesis;

e) providing a second surgical device comprising a second shaft having a length which runs from a first securement end to a second end, the first and second ends of the second shaft defining a second axis which runs through these two end points, wherein at least part of the second shaft is divergent from said second axis; and f) attaching the prosthesis to the securement end and delivering the prosthesis into the acetabulum along the insertion axis while avoiding encroachment on surrounding body parts.

13. The method of claim 12 wherein steps a)-c) are adapted to perform a hip re-surfacing surgery.

14. The method of claim 12 wherein step c) further comprises making a posterior incision that splits the fibers of the gluteus maximus of the patient, anteriorly to their insertion in the ilio-tibial tract.

15. The method of claim 12 wherein the second surgical device of step e) is a pusher and the prosthesis of steps e) and f) is a trial or definitive cemented component.

16. The method of claim 12 wherein the second surgical device of step e) is an impactor and the prosthesis of steps e) and f) is a trial or definitive cementless component.

17. A method for performing a total hip replacement comprising the steps of:
(a) making a posterior incision;
(b) performing a femoral neck osteotomy;
(c) preparing the acetabulum to receive an acetabular cup by reaming the acetabulum with a surgical instrument for acetabular reaming comprising:

providing a surgical device for holding and rotating an acetabular reaming head comprising a drive shaft having a length which runs from a first end to a second end, wherein the first end is adapted for holding an acetabular reaming head, the first and second ends defining an axis which runs through these two end points, wherein said drive shaft comprises a first straight portion, a second straight portion, and an intermediate portion between said first straight portion and said second straight portion;

wherein said first straight portion and said second straight portion are in line with one another and aligned along said axis;

wherein said intermediate portion is permanently divergent from said axis, thereby allowing a head held by the device to access the acetabulum in its true anatomical position while avoiding encroachment of the drive shaft on surrounding body parts; and providing an acetabular reaming head;

wherein the acetabular reaming head is attached to the first end of the surgical device;

(d) securing an acetabular cup in the acetabulum;
(e) preparing the femur to receive a femoral stem; and
(f) securing a femoral stem to the femur.

18. The method of claim 17 wherein in step (d) a device is used comprising a shaft having a length which runs from a first end adapted for holding an acetabular cup, to a second end, the first and second ends defining an axis which runs through these two end points, wherein at least part of the shaft is divergent from said axis.

19. A method for resurfacing a hip joint comprising the steps of:
(a) making a posterior incision;
(b) preparing the acetabulum to receive an acetabular cup by reaming the acetabulum with a surgical instrument for acetabular reaming without fully anteriorly displacing the femoral head; and
(c) securing an acetabular cup in the acetabulum;
wherein said surgical instrument comprises:
a surgical device for holding and rotating an acetabular reaming head comprising a drive shaft having a length which runs from a first end to a second end, wherein the first end is adapted for holding an acetabular reaming head, the first and second ends defining an axis which runs through these two end points;
wherein said drive shaft comprises a first straight portion, a second straight portion, and an intermediate portion between said first straight portion and said second straight portion;
wherein said first straight portion and said second straight portion are in line with one another and aligned along said axis;
wherein said intermediate portion is permanently divergent from said axis, thereby allowing a head held by the device to access the acetabulum in its true anatomical position while avoiding encroachment of the drive shaft on surrounding body parts; and
an acetabular reaming head; and
wherein the acetabular reaming head is attached to the first end of the surgical device.

20. The method of claim 19 wherein in step (c) a device is used comprising a shaft having a length which runs from a first end adapted for holding an acetabular cup, to a second end, the first and second ends defining an axis which runs through these two end points, wherein at least part of the shaft is divergent from said axis.

21. An osteophyte remover instrument for use in removing peripheral acetabulum osteophytes comprising a drive shaft having a first end and a second end, with the drive shaft being connected at the first end to an osteophyte remover head,
wherein said first end and said second end define an axis passing there through;
wherein said drive shaft comprises a first straight portion, a second straight portion, and an intermediate portion between said first straight portion and said second straight portion;
wherein said first straight portion and said second straight portion are in line with one another and aligned along said axis;
wherein said intermediate portion is permanently divergent from said axis, thereby allowing the head to access the acetabulum in its true anatomical position while avoiding encroachment of the drive shaft on surrounding body parts.

22. The instrument of claim 21 wherein the part of the drive shaft that is divergent from the axis is substantially C-shaped or includes a substantially C-shaped section.

23. The instrument of claim 22 wherein the part of the drive shaft that is divergent from the axis forms a C-shape.

24. The instrument of claim 21 wherein the drive shaft is provided with a rotational drive element for rotating the osteophyte remover head.

25. The instrument of claim 24 wherein the rotational drive element is a manual drive element, an air powered drive element or a battery powered rotating drive element.

26. The instrument of claim 24 wherein the rotational drive element is provided with one or more gears.

27. A method for removing peripheral osteophytes from an acetabulum after a cavity has been reamed in said acetabulum, comprising the steps of:
a) providing an osteophyte remover instrument for use in removing peripheral acetabulum osteophytes comprising a drive shaft having a first end and a second end, with the drive shaft being connected at the first end to an osteophyte remover head;
wherein said first end and said second end define an axis passing there through;
wherein said drive shaft comprises a first straight portion, a second straight portion, and an intermediate portion between said first straight portion and said second straight portion;
wherein said first straight portion and said second straight portion are in line with one another and aligned along said axis;
wherein said intermediate portion is permanently divergent from said axis, thereby allowing the head to access the acetabulum in its true anatomical position while avoiding encroachment of the drive shaft on surrounding body parts; and
b) positioning the osteophyte remover head in the cavity, while avoiding encroachment of the instrument on surrounding body parts, and removing peripheral osteophyte from the cavity by rotating the osteophyte remover head in the cavity.

28. A surgical device for holding and rotating an acetabular reaming head, said surgical device comprising:
a drive shaft that permits transmission of torque, said drive shaft having a first end adapted for holding an acetabular reaming head, and a second end;
wherein said drive shaft comprises a first straight portion, a second straight portion, and an intermediate portion between said first straight portion and said second straight portion;
wherein said intermediate portion comprises a first intermediate portion and a second intermediate portion;
wherein said first intermediate portion is closer to said first straight portion than said second intermediate portion;
wherein said second intermediate portion is closer to said second straight portion than said first intermediate portion;
wherein a tangent to a point along said first intermediate portion forms a first angle with an axis defined by said first straight portion, said first angle is greater than zero degrees and less than 180 degrees;
wherein a tangent to a point along said second intermediate portion forms a second angle with said axis, said second angle equals 180 degrees minus said first angle; and
wherein said intermediate portion is permanently divergent from said axis.

29. The device of claim 28 wherein said drive shaft comprises a series of shafts interconnected by universal joints.

30. A surgical device for holding and rotating an acetabular reaming head, said surgical device comprising:
a drive shaft that permits transmission of torque, said drive shaft having a first end adapted for holding an acetabular reaming head, and a second end;
wherein said drive shaft comprises a first straight portion, a second straight portion, and an intermediate portion between said first straight portion and said second straight portion;
wherein said intermediate portion comprises a first intermediate portion and a second intermediate portion;
wherein said first intermediate portion is closer to said first straight portion than said second intermediate portion;

wherein said second intermediate portion is closer to said second straight portion than said first intermediate portion; and wherein said a first intermediate portion bends out of alignment with said first straight portion;

wherein said second intermediate portion bends towards alignment with said first straight portion; and wherein said intermediate portion is permanently divergent from an axis defined by said first straight portion.

31. The device of claim 30 wherein said drive shaft comprises a series of shafts interconnected by universal joints.

32. A method for performing hip surgery on a patient, comprising the steps of:

providing a surgical device for holding and rotating an acetabular reaming head comprising a drive shaft having a length which runs from a first end to a second end, wherein the first end is adapted for holding an acetabular reaming head, the first and second ends defining an axis which runs through these two end points, wherein at least part of the drive shaft is permanently divergent from said axis, allowing a head held by the device to access the acetabulum in its true anatomical position while avoiding encroachment of the drive shaft on surrounding body parts;

providing an acetabular reaming head;

mounting the acetabular reaming head on the first end of the surgical device; and partially anteriorly displacing the femoral head so that the femoral head is not fully anteriorly displaced; and while said femoral head is partially anteriorly displaced, accessing the acetabulum of the patient with the surgical device and reaming the acetabulum with the reaming head.

33. The method of claim 32 further comprising making a posterior incision that splits the fibers of the gluteus maximus of the patient anteriorly to their insertion in the ilio-tibial tract.

34. The method of claim 33 wherein said posterior incision begins at a start distance down from the tip of the greater trochanter, wherein said start distance is equal to a distance from the tip of the greater trochanter to a point of bisection of the lateral cortex.

35. The method of claim 33 wherein said posterior incision extends at an angle of forty to fifty degrees relative to the femoral shaft.

36. The method of claim 33 wherein said posterior incision extends between five and twelve centimeters.

37. The method of claim 33 wherein said posterior incision extends proximally and posteriorly relative to the femoral shaft.

38. The method of claim 32 limited to not incising the ilio-tibial tract.

39. A method for performing hip surgery on a patient, comprising the steps of:

providing a surgical device for holding and rotating an acetabular reaming head comprising a drive shaft having a length which runs from a first end to a second end, wherein the first end is adapted for holding an acetabular reaming head, the first and second ends defining an axis which runs through these two end points, wherein at least part of the drive shaft is permanently divergent from said axis, allowing a head held by the device to access the acetabulum in its true anatomical position while avoiding encroachment of the drive shaft on surrounding body parts;

providing an acetabular reaming head;

mounting the acetabular reaming head on the first end of the surgical device; and partially displacing the femoral head so that the femoral head is not fully displaced; and while said femoral head is partially displaced, accessing the acetabulum of the patient with the surgical device and reaming the acetabulum with the reaming head.

40. The method of claim 39 further comprising making a posterior incision that splits the fibers of the gluteus maximus of the patient anteriorly to their insertion in the ilio-tibial tract.

41. The method of claim 40 wherein said posterior incision begins at a start distance down from the tip of the greater trochanter, wherein said start distance is equal to a distance from the tip of the greater trochanter to a point of bisection of the lateral cortex.

42. The method of claim 40 wherein said posterior incision extends at an angle of forty to fifty degrees relative to the femoral shaft.

43. The method of claim 40 wherein said posterior incision extends between five and twelve centimeters.

44. The method of claim 40 wherein said posterior incision extends proximally and posteriorly relative to the femoral shaft.

45. The method of claim 39 limited to not incising the ilio-tibial tract.

* * * * *